United States Patent [19]

Kuhla et al.

[11] 4,107,430

[45] Aug. 15, 1978

[54] CONVERSION OF TRANS- TO CIS-N,N-DIMETHYL-9-[3-(4-METHYL-1-PIPERAZINYL)PROPYLIDENE]-THIOXANTHENE-2-SULFONAMIDE AND RECOVERY OF THE CIS-ISOMER

[75] Inventors: Donald E. Kuhla, Gales Ferry; Harry A. Watson, Jr., New London, both of Conn.

[73] Assignee: Pfizer Inc., New York, N.Y.

[21] Appl. No.: 734,081

[22] Filed: Oct. 20, 1976

[51] Int. Cl.² ............................................. C07D 409/06
[52] U.S. Cl. ................................. 542/471; 260/328; 260/707
[58] Field of Search ............... 260/240 TC, 707, 328; 542/471

[56] References Cited

U.S. PATENT DOCUMENTS

| 3,115,502 | 12/1963 | Schlapfer et al. | 260/328 |
| 3,310,553 | 3/1967 | Bloom et al. | 260/240 TC |
| 3,514,449 | 5/1970 | Tretter | 424/256 |
| 3,681,346 | 8/1972 | Petersen et al. | 424/250 |

FOREIGN PATENT DOCUMENTS 257,196  1/1963  Australia ........................... 260/240 TC

*Primary Examiner*—Arthur P. Demers
*Attorney, Agent, or Firm*—Connolly and Hutz

[57] ABSTRACT

Trans-N,N-dimethyl-9-[3-(4-methyl-1-piperazinyl)-propylidene]-thioxanthene-2-sulfonamide is isomerized to the cis-isomer by contacting the trans-isomer with strong base in a polar organic solvent. By using an organic solvent in which the solubility of the cis-isomer is substantially less than that of the trans-isomer, the cis-isomer can be selectively precipitated from said solvent, thereby favoring additional isomerization to the cis-isomer in the supernatant, and separated.

8 Claims, No Drawings

CONVERSION OF TRANS- TO CIS-N,N-DIMETHYL-9-[3-(4-METHYL-1-PIPERAZINYL)PROPYLIDENE]-THIOXANTHENE-2-SULFONAMIDE AND RECOVERY OF THE CIS-ISOMER

BACKGROUND OF THE INVENTION

The compound N,N-dimethyl-9-[3-(4-methyl-1-piperazinyl)-propylidene]thioxanthene-2-sulfonamide (known as "thiothixene"), its non-toxic acid addition salts and hydrates of those salts have considerable utility as psychotherapeutic agents in the chemotherapy of certain mental diseases and disorders, especially the treatment of excited mental states. Of particular interest is "thiothixene hydrochloride", the dihydrate of the dihydrochloride acid addition salt of thiothixene. The cis-stereoisomer of thiothixene (melting point = 145°–147° C.), in which the substituted propylidene group is oriented towards the N,N-dimethylsulfonamide group, is far more active pharmacologically than the trans-isomer (melting point = 123°–125° C.).

N,N-dimethyl-9-[3-(4-methyl-1-piperazinyl)-propylidene]-thioxanthene-2-sulfonamide and alternate synthetic methods of preparing it are disclosed in U.S. Pat. Nos. 3,310,553 and 3,354,155. Use of these methods yields a roughly equal mixture of cis- and trans-isomers which, following the teaching of these patents, is converted to isolated cis-isomer by a fractional crystallization method involving repeated partial isomerizations in hydrochloric acid of intermediate crops of trans-isomer. This prior art process for isolating thiothixene in the desired cis-form suffers from several undesirable features: low yield, the need to perform numerous costly and repetitive operations to obtain that yield, the need to precipitate first the undesired steroisomer and then re-dissolve it for conversion to the desired steroisomer, and, finally, the highly unfavorable equilibrium ratio [about 2:1 (trans:cis)] of the aqueous acid steroisomerization of thiothixene. The need for an isomerization/recovery process which would alleviate these undesirable features is manifest.

The conversion of either stereoisomer of a compound of the formula

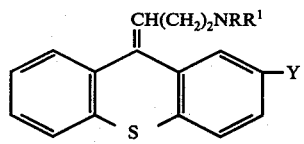

wherein $NRR^1$ can be a heterocyclic ring and Y is halogen, alkyl, hydroxy, alkoxy, alkylthio, acyl, haloalkyl, or amino, to the other stereoisomer by treatment with strong base in a polar organic solvent is disclosed by British Pat. No. 881,488 and Japanese Pat. No. 12,708 (1965). U.S. Pat. No. 3,115,502 indicates general applicability to all geometrically asymmetric 9-(basically substituted)-thioxanthene compounds. This basic isomerization yields an approximately equimolar mixture of the two stereoisomers at equilibrium. After isolation of a portion of the desired isomer by evaporation and selective crystallization, e.g., from petroleum ether, the remaining material containing an excess of the other isomeric form can be subjected once again to the basic conversion reaction. However, numerous cycles of isomerization, evaporation, dilution, selective crystallization, and evaporation and re-dilution of the mother liquor would be required to obtain a substantial isolated yield of the desired isomer.

SUMMARY OF THE INVENTION

Cis-N,N-dimethyl-9-[3-(4-methyl-1-piperazinyl)-propylidene]-thioxanthene-2-sulfonamide is prepared in isolated form by a novel and simplified process which comprises the steps of contacting the trans-isomer with strong base in solution in a reaction-inert polar organic solvent, in which solvent the solubility of the trans-isomer at a temperature of about −15° to 40° C. is at least about 1.25 times that of the cis-isomer, and precipitating and separating said cis-isomer from said solvent at said temperature. The direct precipitation of the cis-isomer from said solvent favors additional conversion of trans-isomer to cis-isomer in the supernatant. The base is selected from the group consisting of alkyl amines of from 3 to 12 carbon atoms, cycloalkyl amines of from 4 to 18 carbon atoms, lithium, sodium and potassium hydroxides, alkoxides of from 1 to 7 carbon atoms, and cycloalkoxides of from 4 to 10 carbon atoms, lithium, sodium and potassium salts of alkyl amines of from 3 to 12 carbon atoms and cycloalkyl amines of from 4 to 18 carbon atoms, and sodium amide.

In a preferred embodiment of the above process, the solvent is selected from the group consisting of acetonitrile, ethyl acetate and N,N-dimethylacetamide, the base is selected from the group consisting of sodium t-butoxide, potassium t-butoxide and, in addition when the solvent is N,N-dimethylacetamide, sodium hydroxide and potassium hydroxide, and the entire process is conducted at a temperature of about −15° C to 40° C. Cis-isomer continuously precipitates directly from the solvent, and as it does so, trans-isomer is simultaneously converted to cis-isomer in the supernatant to an extent of conversion greater than would have been realized in the absence of simultaneous precipitation and isomerization. Thus an excellent yield to isolated cis-isomer crude product can be obtained without the necessity of performing repeated separation, heating, cooling and precipitation steps.

DETAILED DESCRIPTION OF THE INVENTION

The base catalyzed conversion of trans- to cis-N,N-dimethyl-9-[3-(4-methyl-1-piperazinyl)propylidene]thioxanthene-2-sulfonamide behaves like a reversible reaction with an equilibrium ratio in solution of about 45% cis/55% trans. The starting material may be either pure trans-thiothixene or a mixture of cis- and transthiothixene containing a preponderance of the latter. A mixture of the cis- and trans-isomers in approximately equal amounts may also be used as starting material if a means of selectively removing the cis-isomer from solution in the organic solvent at the conversion conditions, e.g. selective precipitation, is provided. The order or addition of thiothixene, base and organic solvent is not critical, but ordinarily it is preferred to first combine thiothixene with the solvent and then add the base. The conversion should be run under anhydrous conditions when necessary to prevent decomposition of the base. At the end of the conversion, water is conveniently added to dilute the base and quench the reaction. In general, any strong base may be used to catalyze the conversion of trans- to cis-thiothixene. Preferably, for reasons of ease in handling and availability, the base is selected from the group consisting of primary, secondary and tertiary alkyl amines of from 3 to 12 total carbon atoms (e.g., t-butylamine, triethylamine, diisopropyl ethyl amine), primary, secondary and tertiary cycloalkyl amines of from 4 to 18 total carbon atoms (e.g., dicyclohexyl amine), the lithium, sodium and potassium salts of these alkyl and cycloalkyl amines, lithium, sodium and potassium hydroxides, alkoxides of from 1 to 7 carbon atoms, and cycloalkoxides of from 4 to 10 carbon atoms, and sodium amide. A more preferred group of bases consists of sodium and potassium hydroxides and alkoxides of from 1 to 7 carbon atoms. A still more preferred group of bases consists of sodium and potassium alkoxides of from 1 to 7 carbon atoms, in particular, sodium and potassium ethoxides, isopropoxides, t-butoxides, t-pentanoates, and 2-hexanoates.

The novel and simplified process for producing cis-N,N-dimethyl-9-[3-(4-methyl-1-piperazinyl)-propylidene]thioxanthene-2-sulfonamide in isolated form significantly reduces the number of operations required to obtain a crude cis-thiothixene product in satisfactory yield. The key to the process is the use of an organic conversion solvent from which cis-thiothixene can be directly and selectively precipitated without substantial precipitation of the trans-isomer. The preferred temperature range for the precipitation and separation steps is about −15° C. to 40° C., because generally reduced solubilities within this range give higher yields. Therefore the organic solvent must be one in which the solubility of trans-thiothixene is substantially greater than, and preferably at least about 1.25 times, the solubility of cis-thiothixene at a temperature of about −15° C. to 40° C. (The scope of this invention includes the use of a solvent which satisfies the above solubility criterion for only some of the temperatures between the −15° C. and 40° C., provided that the precipitation and separation steps are performed within this narrower range of temperatures). Additionally, the solvent must be one in which a catalytically effective amount of base is soluble, since the conversion reaction takes place in liquid solution, and one which does not react excessively with the base or either isomer of thiothixene. Finally, the organic conversion solvent should be polar in nature. A preferred group of polar organic solvents consists of those aromatic and aliphatic ethers, esters, ketones, nitriles, amides, amines, alcohols, alkylsulfoxides and alkylnitro compounds which satisfy the above solubility and inertness criteria. A more preferred group of polar organic solvents consists of those aliphatic ethers, esters, ketones, nitriles, amides and alcohols which satisfy said solubility and inertness criteria. Particularly preferred solvents are acetonitrile, ethyl acetate, N,N-dimethylacetamide, acetone, isopropanol, diisopropyl ether, 1,2-dimethoxyethane and tetrahydrofuran. The most highly preferred solvents are acetonitrile and ethyl acetate. The use of halo-hydrocarbons and aldehydes is generally not favored because of their marked tendency to react with strong bases. It is to be understood that certain materials such as triethylamine can serve as both solvent and base. It is also to be understood that either the solvent or base may be a mixture of substances.

Known methods of optimization can be employed to determine the reaction times and temperatures and concentrations of base required to obtain substantial conversion to the cis-isomer. In general, the rate of conversion in a given solvent/base system will increase as the conversion temperature is increased. The pressure must be sufficient to maintain the reactant in the liquid state, and may be greater than atmospheric. When the base is selected from the group consisting of sodium hydroxide and potassium hydroxide, and the reaction-inert polar organic solvent is selected from the group consisting of alkanols of from 1 to 5 carbon atoms (preferably isopropanol), the conversion is conveniently conducted at reflux under about atmospheric pressure.

The cis-N,N-dimethyl-9-[3-(4-methyl-1-piperazinyl)-propylidene]-thioxanthene-2-sulfonamide free base may be precipitated by any method known to the art, e.g., cooling, evaporation of solvent, addition of a non-solvent for both isomers, or, when feasible, simply allowing the cis-isomer to precipitate from supersaturated solution. The precipitation may be "seeded" to improve product quality by addition of a small quantity of pure cis-isomer solid to supersaturated solution. The precipitated cis-isomer may be separated from the conversion solvent by any known method, e.g., filtration, decantation or centrifugation.

The direct precipitation of the cis-isomer from the conversion solvent provides the opportunity for additional conversion of trans-isomer to take place in the supernatant. However, the conversion and precipitation need not necessarily occur simultaneously. In one embodiment of this novel process (see e.g., Example 8), the conversion is conducted at a relatively high temperature (e.g. reflux) and the cis-thiothixene product precipitated by subsequent cooling to a temperature below the range in which significant conversion takes place. Additional conversion is effected by separating the solids and then re-heating the basified trans-rich mother liquor. Because the solid product crops are precipitated directly from the conversion system and additional conversion conducted in the separated mother liquor, this particular embodiment offers considerable advantages in terms of simplicity of operation over the prior art.

It is to be understood that the scope of the novel process never encompasses a simple recrystallization of cis-thiothixene from a mixture with its trans-isomer. The process of this invention must always include the three steps of conversion, selective precipitation and separation.

In the preferred embodiment of the novel process for producing isolated cis-thiothixene, the base and organic solvent are selected so as to produce strongly basic conversion conditions at temperatures between about −15° C. and 40° C., and the entire process is conducted at a temperature of about −15° C. to 40° C. The solvent is selected from the group consisting of ethykl acetate, acetonitrile and N,N-dimethylacetamide, and the base is selected from the group consisting of sodium t-butoxide, potassium t-butoxide and, in addition when the solvent is N,N-dimethylacetamide, sodium hydroxide and potassium hydroxide. Cis-thiothixene continuously precipitates directly from the organic solvent, and as it does so, trans-isomer is simultaneously converted to cis-isomer in the supernatant to an extent of conversion greater than would have been realized in the absence of simultaneous precipitation and isomerization. Additional conversion begets additional precipitation, and vice versa. Preferably, the total thiothixene concentration should be at least three times the solubility of the cis-isomer in the organic solvent at the conversion temperature actually used.

The total thiothixene charge to said preferred embodiment of the novel process may be either trans-thiothixene, a mixture of cis- and trans-isomers containing a preponderance of the latter, or a mixture having approximately equal amounts of the two isomers. In the latter case it may be desirable to originate precipitation of the cis-isomer, e.g. by seeding, before starting the conversion.

When practicing this preferred embodiment it is desirable to allow the cis-thiothixene to precipitate from supersaturated solution by stirring the conversion mixture within a narrow conversion temperature range (about 10° C. wide), without evaporating solvent, adding a non-solvent, etc., until an apparent equilibrium is reached. The result is a gradual, controlled precipitation of cis-thiothixene, with inclusions of trans-thiothixene minimized. After an apparent equilibrium is reached, additional yield may be obtained by, e.g., evaporation of solvent or cooling.

Particularly surprising and unexpected results are obtained when either ethyl acetate or acetonitrile is used as organic solvent, and either potassium t-butoxide or sodium t-butoxide is used as base, in the preferred embodiment of the novel process for producing isolated cis- N,N-dimethyl-9-[3-(4-methyl-1-piperazinyl)-propylidene]thioxanthene-2-sulfonamide. Transthiothixene can be converted at about 75–80% yield to an isolated cis-thioxthixene first crude crop containing only about 5% trans-isomer and capable of being once-recrystallized to material containing less than 1% trans. The corresponding stereoisomeric distribution ratio of the conversion mixture, including the large bed of precipitated solids, is about 80–85% cis/15–20% trans, an exceedingly favorable ratio. A second crude crop containing about 10% yield can be recovered by processing of the first crop mother liquor.

Said preferred embodiment may be used in conjunction with the synthetic method of preparing thiothixene disclosed in U.S. Pat. No. 3,354,155. In particular, cis-N,N-dimethyl-9-[3-(4-methyl-1-piperazinyl)-propylidene]thioxanthene-2-sulfonamide is prepared in isolated form by a novel and simplified process which comprises the steps of:

a. contacting N,N-dimethyl-9-oxo-thioxanthene-2-sulfonamide with 3-(4-methyl-1-piperazinyl)-propylidene-triphenylphosphorane in an organic solvent to thereby obtain a mixture of cis- and trans-isomers of thiothixene;
b. forming an aqueous solution of the mixture of isomers obtained in (a);
c. basifying said aqueous solution to a pH of about 9 to 14 to extract the aforesaid mixture of isomers into ethyl acetate;
d. treating the ethyl acetate extract with a base selected from the group consisting of sodium t-butoxide and potassium t-butoxide at a temperature of about −15° C. to 40° C; and
e. separating, at a temperature of about −15° C. to 40° C., the cis-isomer which precipitates from said ethyl acetate extract. Acetonitrile may be used in place of ethyl acetate in steps (d) and (e) above, but then, as step (c), the aqueous solution formed in step (b) is basified to a pH of about 9 to 14 to extract the mixture of thiothixene isomers into an organic solvent not fully soluble in water (e.g. methylene chloride), and said organic solvent then removed by evaporation and replaced with acetonitrile.

N,N-dimethyl-9-oxo-thioxanthene-2-sulfonamide can be converted at about 65–70% yield to an isolated cis-thiothixene first crude crop containing only about 5% trans-isomer and capable of being once-recrystallized to material containing less than 1% trans. Two advantages of ethyl acetate are its relatively low solubility in water and its low solubility for triphenylphosphine oxide, a contaminating by-product of the reaction of step (a) (cf. U.S. Pat. No. 3,708,498). The reaction yield in step (a) above is typically about 88–90%.

The following examples illustrate the invention but are not to be construed as limiting the same. Unless otherwise indicated, all cis/trans isomeric ratios were obtained by high pressure liquid chromatography (HPLC) analysis. The chemical name thiothixene refers, of course, to N,N-dimethyl-9-[3-(4-methyl-1-piperazinyl)propylidene]thioxanthene-2-sulfonamide free base.

EXAMPLE 1

A solution of trans-thiothixene (222 mg., 0.50 mmole, 5% cis) and sodium 2-hexanoate (ca. 430 mg., 3.5 mmoles) in diisopropyl ether (15 ml.) was stirred for 72 hours at reflux under nitrogen. Analysis of the reaction solution showed a 48% cis/52% trans ratio of isomers.

EXAMPLE 2

A solution of trans-thiothixene (222 mg., 0.50 mmole, 5% cis) and sodium t-pentanoate (ca. 380 mg., 3.5 mmoles) in acetonitrile (15 ml.) was stirred overnight at room temperature under nitrogen. Analysis of the reaction solution showed a 46% cis/54% trans ratio of isomers.

EXAMPLE 3

A solution of potassium t-butoxide (2 g., 18 mmoles) in t-butyl alcohol (16.5 ml) was added with stirring at −9° C. to 100 ml. of a mixture consisting of cis-thiothixene (3.47 g., 7.8 mmoles), trans-thiothixene (16.2 g., 36.5 mmoles) and acetonitrile. The mixture was then held overnight at −7° C. Analysis of the conversion mixture showed a 79% cis/ 21% trans ratio of isomers.

EXAMPLE 4

Sodium t-butoxide (ca. 2 g., 21 mmoles) was added with stirring at room temperature under nitrogen to a suspension of trans-thiothixene (30 g., 68 mmoles, 6% cis) in acetone (60 ml.), and the mixture stirred for 3.5 hours at room temperature under nitrogen. An additional ca. 2 g. of sodium t-butoxide was then added, and the mixture stirred overnight at room temperature under nitrogen. Water (30 ml.) was then added and the reaction mixture stirred briefly at room temperature. The off-white cis-thiothixene solids were then filtered, washed with acetone/water (1:1), washed with water, and dried (10.5 g., 35% yield, 5% trans, m.p. 145°–147° C.).

EXAMPLE 5

Sodium t-butoxide (ca. 1.2 g., 12.5 mmoles) was added with stirring at room temperature under nitrogen to a suspension of trans-thiothixene (20 g., 45 mmoles, 6% cis) in ethyl acetate (40 ml.), and the mixture stirred for 3.5 hours at room temperature under nitrogen. An additional ca. 1.2 g. of sodium t-butoxide was then added, and the mixture stirred overnight at room temperature under nitrogen. Analysis of the reaction mixture, which contained solids, showed an 84% cis/ 16% trans ratio of isomers. Water (15 ml.) was then added, the reaction mixture stirred briefly at room temperature, and the liquid phases then decanted. The off-white cis-thiothixene solids were triturated with water (70 ml.), filtered, washed with water, and dried (15.3 g., 76.5% yield, 5% trans, m.p. 143°–145° C.).

mained stable at about 40–45% cis/ 55–60% trans throughout the four additional cycles.

| Cycle Number | Combined Filtrate Input (ml.) | Cis/Trans Ratio in Input | Crystallization Volume (ml.)[a] | Crop (g.) | Yield (%) | M.P. (° C.) | % Trans in crop |
|---|---|---|---|---|---|---|---|
| 2 | 300[b] | 21.5/78.5 | 250 | 6.8 | 27.2 | 142–144 | 17.5 |
| 3 | 250[c] | 26/74 | 150 | 1.95 | 7.8 | 143–145 | 13 |
| 4 | 100[b] | 31.5/68.5 | 100 | 1.43 | 5.7 | 142–145 | 17 |
| 5[d] | 100[c] | 27/73 | 75 | 0.92 | 3.7 | 143.5–146 | 10 |

[a]Total filtrate from filtration and wash of carbon-Super-Cel cake evaporated in vacuo before precipitation of solids
[b]After evaporation in vacuo
[c]No evaporation of combined filtrate performed
[d]Basified input refluxed for 16 hours
Total yield of off-white crude cis-thiothixene = 38.0% + 27.2% + 7.8% + 5.7% + 3.7% = 82.4%

EXAMPLE 6

In like manner to that described in Example 5, off-white cis-thiothixene solids (81% yield, 5% trans, m.p. 143°–145° C.) were prepared by using potassium t-butoxide as base and ethyl acetate as solvent. The ratio of isomers in the reaction mixture, which contained solids, was 83% cis/ 17% trans.

EXAMPLE 7

Powdered potassium hydroxide (ca. 0.3 g., 5.3 mmoles) was added with stirring at 0° C. under nitrogen to a solution of trans-thiothixene (20.67 g., 47 mmoles, ca. 16% cis) in N,N-dimethylacetamide (42.7 ml.), and the mixture stirred for 90 minutes at 0° C. under nitrogen. A second ca. 0.3 g. potassium hydroxide addition was made during this stirring period (at 60 minutes) and a third ca. 0.3 g. addition at the end of the period. The mixture was then held overnight at 3° C. under nitrogen. The solids which precipitated were filtered from the reaction mixture, washed with one-half of the filtrate, and washed with N,N-dimethylacetamide. Analysis of the filtrate showed a ca. 50% cis/ 50% trans ratio of isomers. The solids were then triturated with water (250 ml.), and an off-white cis-thiothixene crop filtered and dried (9.02 g., 44% yield, 8% trans, m.p. 138°–144° C.).

EXAMPLE 8

A solution of trans-thiothixene (25 g., 56.35 mmoles, 10% cis) and potassium hydroxide (250 mg., 4.46 mmoles) in isopropanol (300 ml.) was refluxed with stirring for 4.5 hours. Analysis of the reaction solution showed at 44% cis/ 56% trans ratio of isomers. The solution was then treated with Darco G-60 activated carbon (Atlas Chemical Industries, Inc., Wilmington, Del.), the mixture of solution and carbon stirred briefly at reflux, and the mixture then hot filtered through Super-Cel (Johns-Mansville Corp., Lompoc. Calif.). The filter cake was washed with hot isopropanol (75 ml.), and the total filtrate cooled to room temperature, seeded with pure cis-thiothixene and then stirred overnight at room temperature. The off-white cis-thiothixene solids which precipitated were filtered, washed with isopropanol and dried (9.5 g., 38.0% yield, 19% trans, m.p. 141°–143.5° C.).

The combined filtrate from the first crop filtration and wash was evaporated in vacuo to 300 ml. and then treated in like manner to that described in the preceeding paragraph. This process was continued until a total of five crops had been taken. The potassium hydroxide charge to each of cycles 2 through 5 was about 1 mg. per ml. combined filtrate from the preceeding cycle (after evaporation, if conducted, of said combined filtrate). The ratio of isomers in the reaction solution re- The combined crude crop from the first and second cycles was triturated in water (200 ml.), filtered, and washed with water. The wet cake was then recrystallized from acetonitrile (72.4% recrystallization yield, ~1% trans by paper chromatography, m.p. 145°–148° C., NMR and IR spectra superimposable upon analytical standards, elemental analysis calculated: 62.27% C; 6.59% H; 9.47% N; found: 62.46% C; 6.63% H; 9.35% N).

In like manner the combined curde crop from the third and fourth cycles was recrystallized (64% recrystallization yield, ~1% trans by paper chromatography and HPLC, m.p. 146°–149° C.).

In like manner the crude crop from the fifth cycle was recrystallized (m.p. 146°–148.5° C., elemental analysis calculated: 62.27% C; 6.59% H; 9.47% N; found: 62.55% C; 6.52% H; 9.54% N).

Significant additional amounts of thiothixene remained in the fifth crop crude precipitation and three recrystallization filtrates.

EXAMPLE 9

5N aqueous sodium hydroxide was added to a suspension of thiothixene.$2H_3PO_4$ (63.96 g., 100 mmoles, ca. 85% trans/ 15% cis) in water (750 ml.)/methylene chloride (750 ml.) until the aqueous phase was strongly basic. The phases were separated and the aqueous phase extracted with an additional 200 ml. portion of methylene chloride. The combined methylene chloride extract was dried ($Na_2SO_4$), filtered and evaporated in vacuo to a light brown oil (ca. 45 g., ca. 100% yield, ca. 85% trans/15% cis). The oil was dissolved in warm acetonitrile (100 ml.) and the solution cooled to room temperature. Some solids, probably trans-thiothixene, formed upon cooling. Potassium t-butoxide (1.1 g., 9.8 mmoles) was added and the mixture stirred overnight at room temperature. Analysis of the reaction mixture, which contained solids, showed a ca. 85% cis/ 15% trans ratio of isomers. Water (10 ml.) was then added and the reaction mixture stirred briefly at room temperature. The tan cis-thiothixene solids were then filtered, washed with acetonitrile, and dried (35.0 g., 78.9% yield, 5% trans, m.p. 143°–145° C.).

The combined filtrate from the first crop filtration and wash was evaporated to dryness in vacuo and dissolved in methylene chloride (300 ml.), and the resulting solution extracted with 3N hydrochloric acid (2 × 300 ml.). The combined aqueous extract was washed with methylene chloride (100 ml.) and then basified with 5N aqueous sodium hydroxide. A brown oil formed upon basification which was separated, and dissolved in methylene chloride (500 ml.). The resulting solution was dried ($MgSO_4$), filtered and evaporated in vacuo to a brown foam. Analysis of this foam showed a 58% cis/ 42% trans ratio of isomers. The foam was dissolved in dry acetonitrile (30 ml.), and the solution seeded with cis-thiothixene and stirred for 30 minutes at room temperature, by which time precipitation of solids had begun. Potassium t-butoxide (400 mg., 3.6 mmoles) was then added and the mixture stirred overnight at room temperature. Analysis of the reaction mixture, which contained solids, showed a 61% cis/39% trans ratio of isomers. Water (1 ml.) was then added and the reaction mixture stirred briefly at room temperature. The tan cis-thiothixene solids were then filtered and dried (4.0 g., 9.0% yield, 5% trans, m.p. 142–144.5° C.). Total yield to crude cis-thiothixene solids was 87.9%.

The first crop crude cis-thiothixene (35.0 g., 78.9 mmoles) was triturated with water (200 ml.) to remove any residual base, filtered, washed with water, and air dried for 30 minutes. While still slightly wet it was dissolved in acetonitrile (250 ml.) and, after charcoal treatment, recrystallized (25.7 g., 57.9% yield, <1% trans, m.p. 146°–147.5° C., NMR and IR spectra superimposable upon analytical standards, elemental analysis calculated: 62.27% C; 6.59% H; 9.47% N; found: 62.35% C; 6.65% H; 9.51% N). A second crop of recrystallized cis-thiothixene was precipitated by evaporating the first crop recrystallization acetonitrile filtrate in vacuo to about 75 ml. (5.9 g., 13.3% yield, 1–2% trans, m.p. 145°–147° C.

Total yield for this example was thus 71.2% to once recrystallized white cis-thiothixene solids plus another 9.0% to the second crop crude cis-thiothixene. Significant additional amounts of thiothixene remained in the second crop crude precipitation and second crop recrystallization filtrates.

EXAMPLE 10

N-butyl lithium (69 ml. of a 2.4 molar hexane solution, 166 mmoles) was added over a 15 minute period with vigorous stirring under nitrogen to a suspension of 3-(4-methyl-1-piperazinyl) propyltriphenylphosphonium bromide hydrobromide (46.5 g., 82.4 mmoles) in tetrahydrofuran (250 ml.). The exothermic reaction temperature was maintained at 55° C. during this period by regulating the rate of addition of n-butyl lithium. The mixture was then refluxed with stirring (for about 1.5 hours) under nitrogen until a complete red solution was obtained.

EXAMPLE 11

The reaction solution from Example 10 was cooled to room temperature, and N,N-dimethyl-9-oxo-thioxanthene-2-sulfonamide (24 g., 75 mmoles) added over a five minute period with stirring under nitrogen. The resulting reddish-brown solution was refluxed with stirring for 16 hours under nitrogen, and then cooled to room temperature. Water (50 ml.) was added, and the reaction mixture stirred briefly and then evaporated in vacuo. The resulting two-phase mixture was stirred at room temperature with water (500 ml.) and ethyl acetate (500 ml.), the liquid phases separated, and the aqueous layer extracted again with fresh ethyl acetate (2 33 200 ml.). The combined ethyl acetate extract was stirred at room temperature with water (500 ml.), the pH of the aqueous phase adjusted to 1.5 with 6N hydrochloric acid, the liquid phases separated, and the aqueous layer washed with fresh ethyl acetate (2 × 200 ml.).

The aqueous layer was then stirred at room temperature with fresh ethyl acetate (500 ml.), the pH of the aqueous phase adjusted to 11 with 5N aqueous sodium hydroxide, the liquid phases separated, and the aqueous layer extracted again with fresh ethyl acetate (2 × 200 ml.). The combined ethyl acetate extract was stirred at room temperature with sodium sulfate and Darco G-60 activated carbon, the mixture filtered through SuperCel, and the filter cake washed with ethyl acetate (100 ml). The total filtrate was evaporated in vacuo to about 90 ml. Potassium t-butoxide (2 g., 18 mmoles) was added with stirring at room temperature under nitrogen to the concentrated filtrate, and the mixture stirred for 3.5 hours at room temperature under nitrogen. An additional 2 g. potassium t-butoxide was then added, and the mixture stirred for another 16 hours at room temperature under nitrogen. Analysis of the reaction mixture, which contained solids, showed an 87% cis/ 13% trans ratio of isomers. Water (22 ml.) was then added, the reaction mixture stirred briefly at room temperature, and the liquid phases then decanted. The off-white cis-thiothixene solids were triturated with water (100 ml.), filtered, washed with water, and dried (22 g., 66% yield, 5% trans, m.p. 142°–144° C.

What is claimed is:

1. A process for the preparation of the cis-isomer of N,N-dimethyl-9-[3-(4-methyl-1-piperazinyl)-propylidene]thioxanthene-2-sulfonamide in isolated form which comprises the steps of contacting the trans-isomer with a base, selected from the group consisting of alkyl amines of from 3 to 12 total carbon atoms; cycloalkyl amines of from 4 to 18 total carbon atoms; lithium, sodium and potassium hydroxides, alkoxides of from 1 to 7 carbon atoms, and cycloalkoxides of from 4 to 10 carbon atoms; lithium, sodium and potassium salts of alkyl amines of from 3 to 12 total carbon atoms and cycloalkyl amines of from 4 to 18 total carbon atoms; and sodium amide, in solution in a reaction-inert polar organic solvent, in which solvent the solubility of the transisomer at a temperature of about −15° C. to 40° C. is at least about 1.25 times that of the cis-isomer, and separating precipitated cis-isomer from said solvent at said temperature.

2. The process of claim 1 wherein said base is selected from the group consisting of sodium hydroxide and potassium hydroxide, and said solvent is selected from the group consisting of alkanols of from 1 to 5 carbon atoms, said trans-isomer being contacted with said base in solution in said solvent at reflux under about atmospheric pressure.

3. The process of claim 2 wherein said solvent is isopropanol.

4. A process for the preparation of the cis-isomer of N,N-dimethyl-9-[3-(4-methyl-1-piperazinyl)-propylidene]thioxanthene-2-sulfonamide in isolated form which comprises the steps of contacting the trans-isomer with a base, selected from the group consisting of sodium hydroxide, potassium hydroxide, sodium t-butoxide and potassium t-butoxide, in solution in a solvent selected from the group consisting of ethyl acetate, acetonitrile and N,N-dimethylacetamide, and separating from said solvent the cis-isomer which precipitates, said preparation being conducted at a temperature of about −15° C. to 40° C., and said solvent being N,N-dimethylacetamide when said base is sodium hydroxide or potassium hydroxide.

5. The process of claim 4 wherein said solvent is acetonitrile.

6. The process of claim 4 wherein said solvent is ethyl acetate.

7. In a process for the preparation of the cis-isomer of N,N-dimethyl-9-[3-(4-methyl-1-piperazinyl)-propylidene]thioxanthene-2-sulfonamide in isolated form which comprises the steps of:
   a. contacting N,N-dimethyl-9-oxo-thioxanthene-2-sulfonamide with 3-(4-methyl-1-piperazinyl)-propylidene-triphenylphosphorane in an organic solvent to thereby obtain a mixture of cis- and trans-isomers of N,N-dimethyl-9-[3-(4-methyl-1-piperazinyl)-propylidene]thioxanthene-2-sulfonamide;
   b. forming an aqueous solution of the mixture of isomers obtained in (a);
   c. basifying said aqueous solution to a pH of about 9 to 14 to extract the aforesaid mixture of isomers into an organic solvent; and
   d. isolating said cis-isomer from said organic solvent extract, the improvement which comprises using ethyl acetate as said organic solvent in steps (c) and (d), and isolating said cis-isomer from the ethyl acetate extract by treating said extract with a base selected from the group consisting of sodium t-butoxide and potassium t-butoxide at a temperature of about −15° C. to 40° C., and separating, at a temperature of about −15° C. to 40° C., the cis-isomer which precipitates from said ethyl acetate extract.

8. In a process for the preparation of the cis-isomer of N,N-dimethyl-9-[3-(4-methyl-1-piperazinyl)-propylidene]thioxanthene-2-sulfonamide in isolated form which comprises the steps of:
   a. contacting N,N-dimethyl-9-oxo-thioxanthene-2-sulfonamide with 3-(4-methyl-1-piperazinyl)-propylidene-triphenylphosphorane in an organic solvent to thereby obtain a mixture of cis- and trans-isomers of N,N-dimethyl-9-[3-(4-methyl-1-piperazinyl)propylidene]thioxanthene-2-sulfonamide;
   b. forming an aqueous solution of the mixture of isomers obtained in (a);
   c. basifying said aqueous solution to a pH of about 9 to 14 to extract the aforesaid mixture of isomers into an organic solvent; and
   d. isolating said cis-isomer from said organic solvent extract, the improvement which comprises isolating said cis-isomer from said organic solvent extract by removing said organic solvent by evaporation and replacing it with acetonitrile, treating the resulting acetonitrile solution with a base selected from the group consisting of sodium t-butoxide and potassium t-butoxide at a temperature of about −15° C. to 40° C., and separating, at a temperature of about −15° C. to 40° C., the cis-isomer which precipitates from said acetonitrile solution.

* * * * *